US006547748B1

(12) United States Patent  (10) Patent No.: US 6,547,748 B1
Shine  (45) Date of Patent: Apr. 15, 2003

(54) PHYSIOLOGICAL EVENT DETECTOR AND METHOD OF OPERATING THE SAME

(75) Inventor: David J. Shine, Hamden, CT (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 0 days.

(21) Appl. No.: 09/640,577

(22) Filed: Aug. 17, 2000

(51) Int. Cl.$^7$ ........................... A61B 5/103; A61B 5/117
(52) U.S. Cl. ..................................................... 600/588
(58) Field of Search ................................. 600/588, 546, 600/551, 595, 587, 596

(56) References Cited

U.S. PATENT DOCUMENTS

| 3,989,034 A | | 11/1976 | Hojaiban |
| 5,301,680 A | * | 4/1994 | Rosenberg ................. 600/546 |
| 6,093,151 A | | 7/2000 | Shine et al. |
| 6,134,466 A | * | 10/2000 | Rosenberg ................. 600/546 |

FOREIGN PATENT DOCUMENTS

| EP | 0 808 603 A2 | 11/1997 |
| WO | WO 93/09712 | 5/1993 |
| WO | WO 96/15713 | 5/1996 |
| WO | WO 99/19704 | 4/1999 |

OTHER PUBLICATIONS

Boos, A. et al.; A New, Lightweight Fetal Telemetry System; Hewlett–Packard Journal, Hewlett–Packard Company; XP000581129; Dec. 1, 1995; pp. 82–93; vol. 46, No. 6; Palo Alto, United States.

* cited by examiner

Primary Examiner—Max F. Hindenburg
Assistant Examiner—Brian Szmal
(74) Attorney, Agent, or Firm—Michael Best & Friedrich LLP

(57) ABSTRACT

A method and apparatus for detecting a physiological signal and for providing indication of an event relating to the physiological signal. The apparatus including an input terminal for connection to a patient to acquire a physiological signal having at least one physiological event, an analysis module having a processor and software for operating the processor to determine an occurrence of the event and to generate a signal upon the occurrence of the event, and an indicator that receives the signal and provides to a user an indication of the event in response to the signal. The method including obtaining the physiological signal, determining the onset of the physiological event, and generating a signal in response to the onset of the physiological event.

19 Claims, 2 Drawing Sheets

PHYSIOLOGICAL EVENT DETECTOR AND METHOD OF OPERATING THE SAME

BACKGROUND OF THE INVENTION

The invention relates to a monitoring device and, particularly, to a monitoring device for detecting physiological events and for generating an audio and/or visual indication of the occurrence of the physiological event.

A tocodynamometer ("toco") or a uterine pressure catheter are commonly used to collect uterine activity or contraction data during a birthing event. In the case of a toco, the transducer is attached to a belt that is strapped to the mother's abdomen. During a uterine contraction, the transducer is pressed between the abdomen and the belt and a contraction is registered. In the case of the intrauterine pressure catheter, an intrauterine pressure sensor is inserted by catheter through the birth canal and into the uterus. The sensor registers the change in uterine pressure that occurs during a contraction.

A signal from the toco or IUP transducer is referred to as a uterine activity signal, which may contain information indicative of uterine contractions. The uterine activity signal is sampled by the fetal monitor and plotted or trended over time on a strip chart. Uterine contractions appear as humps in the waveform shown on the strip chart. Alternatively, the maternal/fetal monitor can visually display a portion of the uterine activity waveform on a monitor screen as well as displaying an instantaneous pressure.

Another sensor that may be used during a birthing event is a fetal pulse oxygen saturation ("FSpO2") sensor. The FSpO2 sensor utilizes an infrared sensor to measure an amount of oxygen within a patient's blood. During a birthing event, the FSpO2 sensor is inserted by catheter through the birth canal into the uterus and measures the amount of oxygen within a fetus' blood while the fetus is in the mother's uterus.

SUMMARY OF THE INVENTION

The invention provides a means for informing a clinician of when a uterine contraction is beginning or ending. This information is important when inserting or repositioning the FSpO2 sensor. Inserting or repositioning the FSpO2 sensor while a uterine contraction is occurring may result in loss of data and added patient discomfort. The invention is an improvement over prior art monitors because the clinician does not need to be looking at the monitor display or at the strip chart to determine if a contraction is occurring. An audio indicator on the user interface of the monitor would alert the clinician as to the onset of a uterine contraction.

Another problem that arises with prior art maternal/fetal monitors is that the trending of the strip chart is a retrospective interpretation of the birthing event. Due to the low trending rate of the strip chart, it may be unclear whether a uterine contraction is occurring without a physical examination. Moreover, the clinician must visually inspect the strip chart for a period of time and compare the currently sampled data with previous baseline data to determine if a contraction is occurring. Thus, the clinician may not be certain that a uterine contraction is beginning.

For example, if the mother is under epidural or some other anesthesia, she may not be aware that a contraction is occurring. In addition, if the clinician is not continuously inspecting the strip chart pressure display, or the material abdomen, then the clinician may also not be aware that a contraction is occurring. This may result in the clinician informing the patient to contract uterine and vaginal muscles (i.e., "push") at an improper time. By providing an indicator, the clinician can be more informed as to when a contraction is occurring and, therefore, can inform the laboring mother to "push" at the proper time during the contraction.

Accordingly, the invention provides a medical device, including an input terminal for connection to a patient to acquire a uterine activity signal having at least one uterine contraction, an analysis module including a processor and software for operating the processor to determine an occurrence of an event relating to the uterine contraction and to generate a signal upon the occurrence of the event, and an indicator that receives the signal and provides to a user an indication of the event in response to the signal. The indicator may be a visual indicator or an audible indicator.

In a first embodiment, the software further operates the processor to determine a second event relating to the uterine contraction, and to generate a second signal upon the occurrence of the second event. In addition, the indicator receives the second signal and provides to a user an indication of the second event in response to the signal.

In a second embodiment, the software further operates the processor to determine a second event relating to the uterine contraction, and to terminate generation of the signal upon the occurrence of the second event.

In a third embodiment, the software operates the processor to determine when a maximum amplitude of the uterine contraction occurs, and to generate a second signal upon occurrence of the maximum amplitude. In addition, the indicator receives the second signal and provides to a user an indication of the maximum amplitude in response to the second signal. Furthermore, for the third embodiment, the software operates the processor to determine a second event relating to the uterine contraction, and to generate a third signal upon the occurrence of the second event. The indicator receives the third signal and provides to a user indication of the second event.

The invention further provides a medical device for acquiring and analyzing a physiological signal having at least one physiological event. The medical device includes an input terminal for connection to a patient to acquire the physiological signal, means for a determining the beginning of the physiological event and for generating a signal indicating the beginning of the physiological event, and an indicator that receives the signal and provides to a user an indication of the beginning of the physiological event in response to the signal.

The invention further provides a method of analyzing a physiological signal based on at least one physiological event. The method comprises the acts of obtaining the physiological signal, determining the onset of the physiological event, and generating a signal in response to the onset of the physiological event.

The invention further provides a method of notifying a clinician to instruct a patient to perform an action during a birthing event. The method includes the acts of providing a medical device including a uterine activity sensor, an analysis module and an indicator; attaching the uterine activity sensor to the patient; acquiring a uterine activity signal from the patient with the uterine activity sensor, the uterine activity signal having at least one uterine contraction; determining an occurrence of an event relating to the uterine contraction with the analysis module; generating an indicator signal with the analysis module upon the occurrence of the event; providing the indicator signal to the indicator; and instructing the patient to perform an action in response to the signal being provided to the indicator.

Other features and advantages of the invention will become apparent to those skilled in the art upon review of the following detailed description, claims, and drawings.

DETAILED DESCRIPTION

Before one embodiment of the invention is explained in full detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including" and "comprising" and variations thereof herein is meant to encompass the items listed thereafter and equivalents thereof as well as additional items.

Figure 1:
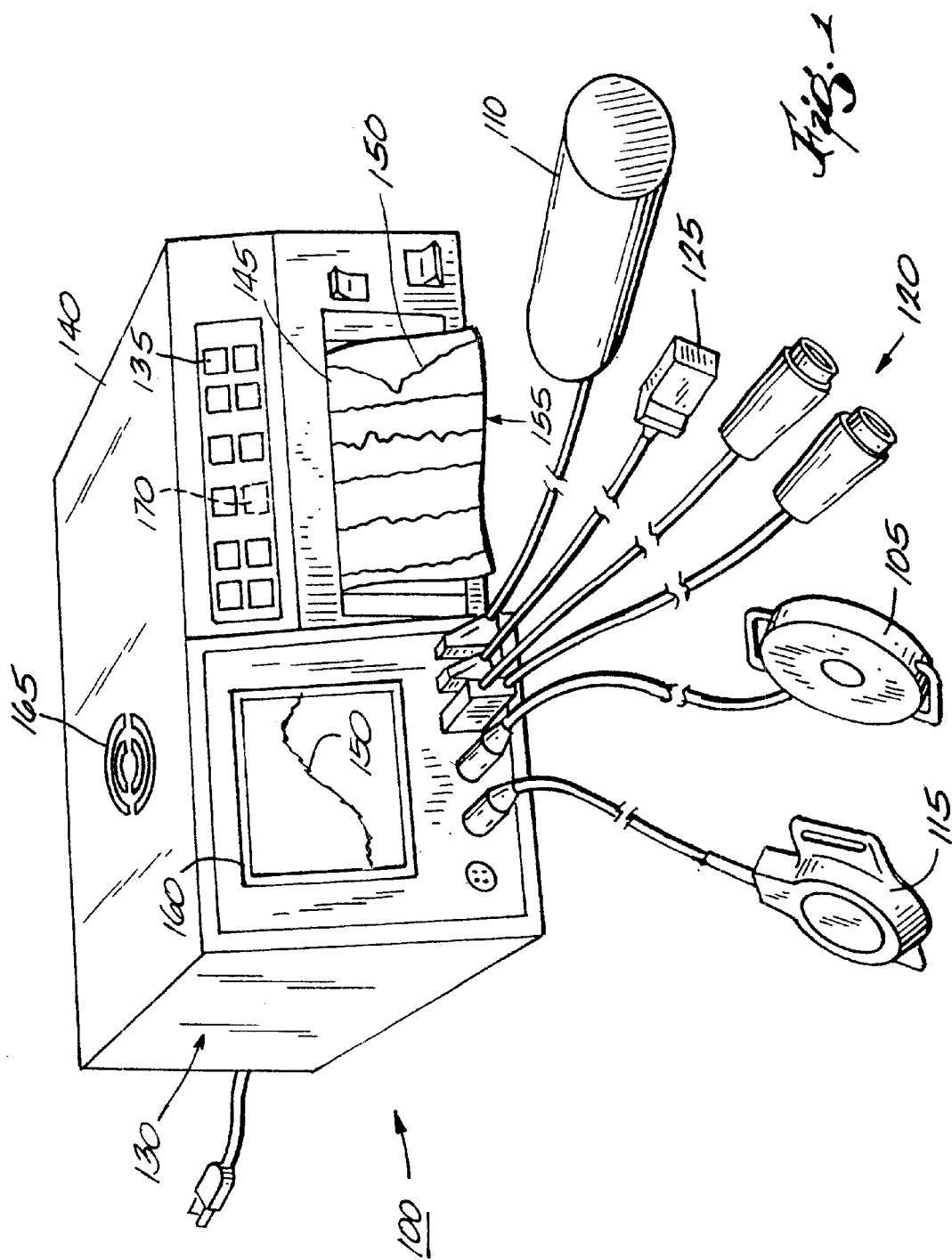
FIG. 1 is a perspective view of a maternal/fetal monitor embodying the invention.
Figure 2:
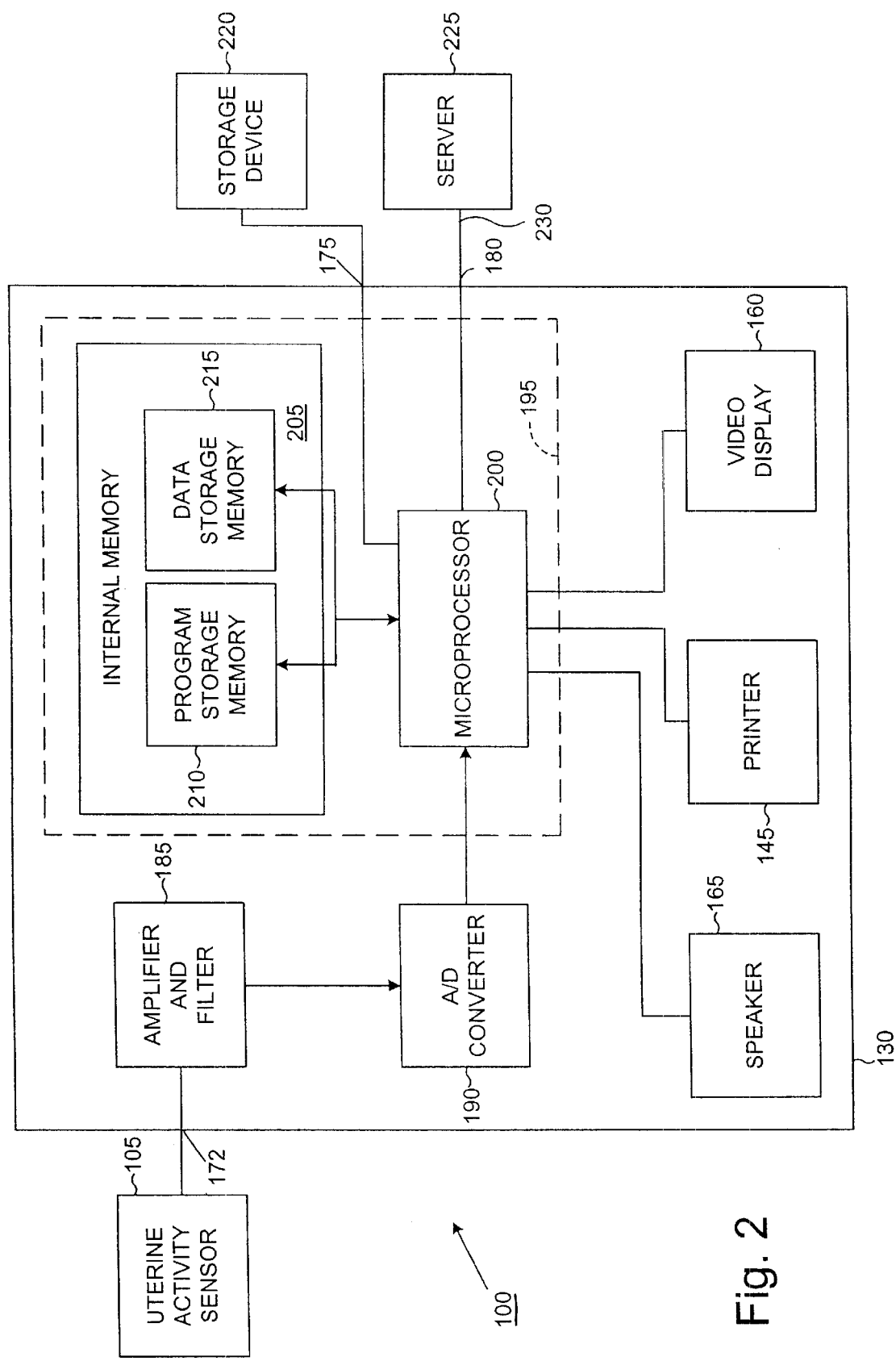
FIG. 2 is a schematic of the maternal/fetal monitor embodying the invention.

Shown in FIG. 1 and schematically represented in FIG. 2 is a maternal/fetal monitor 100 embodying the invention. In general terms, the monitor 100 includes one or more sensors 105, 110, 115, 120, 125 and a central processing unit 130.

As shown in FIG. 1, the monitor 100 includes a uterine activity sensor 105, which may be any well-known uterine activity sensing device. In FIG. 1, the uterine activity sensor 105 is shown as a tocodynamometer ("toco"). The toco is a transducer attached to a belt (not shown) that is strapped to the mother's abdomen. Once the toco belt is strapped to the mother's abdomen, the transducer obtains a "raw" uterine activity signal from the mother, and a clinician pushes a button 135 on the monitor 100 to set a baseline for an algorithm used by the central unit 130.

The uterine activity sensor may also be an intrauterine pressure catheter (not shown). The intrauterine pressure catheter is inserted transcervically into the uterine cavity to measure intrauterine pressure. The catheter may be a fluid-filled catheter or a transducer-tipped catheter. Once the intrauterine pressure catheter is positioned in the uterine cavity, the clinician pushes the button 135 on the monitor 100 to set a baseline for the algorithm used by the central unit 130. The catheter records relative changes in intrauterine pressure from the baseline caused by uterine contractions. Thus, the catheter also obtains a "raw" uterine activity signal from the mother.

The monitor 100 may also include a non-invasive blood measuring device 110, an ultrasonic sensor 115, fetal and maternal ECG sensors 120, and fetal and maternal pulse oximetry sensors 125. The sensors are all conventional and need not be discussed in detail for purposes of understanding the present invention. In addition, other sensors can be added to the monitor 100.

The monitor 100 includes a central processing unit 130 having a housing 140 The central processing unit 130 further includes a conventional strip chart recorder 145 mounted in the housing 140. The conventional strip chart 145 displays data in the form of a continuous uterine activity waveform 150 on a paper strip chart 155. The central processing unit 130 further includes a visual display 160 mounted in the housing 140. The display 160 can also display the uterine activity waveform 150.

The central processing unit 130 further includes an audible speaker 165 capable of providing audible sounds or audible indication to a clinician. As an alternative or in addition to the audible speaker 165, the central unit 130 may further include a visual indicator capable of providing visual indication to a clinician. The visual indicator may be displayed on the visual display 150 as an icon, be the visual display 150 changing contrast or background colors, or be a light-emitting diode 170 (shown in phantom).

Referring to FIG. 2, the central processing unit 130 further includes input terminal 172 and output terminals 175 and 180. Additional terminals may be added as needed. Input terminal 172 provides an interface between the uterine activity sensor 105 and the central processing unit 130.

The central processing unit 130 further includes an amplifier and filter 185 connected to the input terminal 172. The amplifier and filter 185 receives the "raw" uterine activity signal from the input terminal 172, and amplifies and filters the data to create an analog uterine activity signal. The central processing unit 130 further includes an analog-to-digital (A/D) converter 190 electrically connected to the amplifier and filter 185. The A/D converter 190 receives the analog uterine activity signal and converts the analog uterine activity signal to a digital uterine activity signal.

The central processing unit 130 further includes a means for determining a beginning of a physiological event and for generating a signal indicating the beginning of the physiological event. Additionally, the central processing unit 130 includes an analysis 195 for determining an ending of the physiological event, for generating a second signal indicating the ending of the physiological event, for determining when a maximum amplitude of a physiological event occurs, and for generating a third signal indicating the maximum amplitude occurred. As shown in FIG. 2, the analysis module 195 is electrically connected to the A/D converter 190. The analysis module 195 reads the digital uterine activity signal at a given sampling rate and determines whether a uterine contraction is occurring. The analysis module 195 includes a processor 200 and internal memory 205. The internal memory 205 includes program storage memory 210 for storing a software program and data storage memory 215 for storing sampled data. In other embodiments, the analysis module may be an application specific integrated circuit ASIC (not shown).

As shown in FIG. 2, output units 220 and 225 are connected to the central unit 130 at output terminals 175 and 180. The output units include a storage device 220 (e.g., magnetic disc drive, read/write CD-ROM, etc.), and a server 225 or other processing unit (e.g., a personal computer). The server 225 is connected via a distributed network 230. Of course other output units can be attached. In addition, the output units may be incorporated within the central unit 130, or the printer 145 and display 160 can be separate from the central unit 130. Moreover, not all of the output units shown are required for operation of the monitor 100.

In operation, the uterine activity sensor 105 is connected to a patient and detects uterine activity resulting in a "raw" uterine activity signal. The raw uterine activity signal is provided to the central unit 130 at input terminal 172. The raw uterine activity data enters the central unit 130 and is provided to the amplifier and filter 185. The amplifier and filter 185 amplifies and filters the raw uterine activity signal by removing other biological signals and noise signals. The resulting signal from the amplifier and filter is an analog uterine activity signal.

The resulting uterine activity signal is provided to the A/D converter 190. The A/D converter 190 samples the analog uterine activity signal to create a digital uterine activity signal and provides the digital uterine activity signal to the analysis module 195. The analysis module 195 acquires the digitally sampled uterine activity signal from the A/D converter 190 and implements a software-based program for analyzing the acquired uterine activity signal.

While implementing the program, the analysis module determines an occurrence of a first event relating to the uterine contraction and determines the occurrence of a second event relating to the uterine contraction. For example, the first event may be an onset or beginning of a uterine contraction, and the second event may be a termination or ending of the uterine contraction.

The occurrence of events relating to the uterine contraction may be determined by analysis module 195 in any well-known manner. In the embodiment shown in the drawings, the analysis module 195 detects the occurrence of contractions by using an algorithm to calculate the change in incremental slope of the uterine activity data signal over time. One such algorithm is disclosed in U.S. Pat. No. 3,989,034, which is incorporated herein by reference. The algorithm preferably calculates the incremental slope of the uterine activity signal in real time. Once the incremental slope rises to a predetermined level above a baseline value, the software determines a uterine contraction has begun. As the contraction is beginning, the microprocessor generates an indication signal that is provided to a visual and/or audio indicator. For example, the software may provide the indication signal to the speaker 165 resulting in an audible noise. Alternatively, the microprocessor may provide the indication signal to the LED 170 resulting in the LED 170 providing visual indication. Even further, the microprocessor may provide the indication signal to the visual display 160 resulting in the visual display providing visual indication. The visual indication resulting from the visual display 160 may be a visual display icon or may be the display changing contrast or background color in a flashing or non-flashing sequence.

Once the first audio and/or visual indication occurs, the clinician may inform he mother to contract her uterine and vaginal muscles (i.e., "begin pushing"). Alternatively, if the clinician is inserting or reposition a sensor within the mother's uterus, the clinician may temporarily stop the procedure once the audio and/or visual indication occurs.

In one embodiment of the invention, the microprocessor generates the audio and/or visual indication for a period of time (e.g., approximately 2 seconds). The program continues to register incremental changes during the generation of the indicator until it registers a completion of the uterine contraction. For example, after the microprocessor determines a maximum amplitude occurs, the microprocessor will examine incremental slope declines until the incremental slope stabilizes at a baseline value. Once the incremental slope has stabled, the software determines the uterine contraction has ended. After the ending of the uterine contraction has occurred, the software generates a second indication signal that is provided to the visual/and or audio indicator as is disclosed above. Preferably, the first and second indication signals result in first and second audible chimes, respectively, where the first and second chimes have different tones. The clinician can then tell the mother to stop contracting her uterine and vaginal muscles (i.e., "stop pushing") or can again reinsert or reposition the intrauterine sensor.

In a second embodiment, the microprocessor continuously generates the indication signal until the software determines the uterine contraction has terminated or ended. Once the software determines the contraction has terminated, the microprocessor ceases generation of the indication signal.

In a third embodiment, the microprocessor 200 generates the first indication signal for either a finite period of time or until a maximum amplitude of the uterine contraction occurs. Once the software determines the maximum occurs, the microprocessor generates a second indication signal resulting in a second audio and/or visual indication. The microprocessor generates the second indication signal for either a finite period of time or until the termination of the uterine contraction. Once the termination occurs, the software generates a third visual indication signal resulting in a third audio and/or visual indication. The microprocessor generates the third indication signal for either a finite period of time or until the next contraction occurs.

As can be seen from the above, the present invention provides a medical device that detects uterine contractions and generates an audio/visual indicator of when a contraction is beginning and/or ending. Of course the invention can be extended to other physiological signals that include physiological events. Various features and advantages of the invention are set forth in the following claims.

What is claimed is:

1. A medical device, comprising:

an input terminal for connection to a patient to acquire a uterine activity signal comprising a uterine contraction;

an analysis module comprising a processor and software for operating the processor to determine a change in incremental slope of the uterine activity signal, to determine an indication of an event relating to the uterine contraction based on the change in incremental slope, and to generate a signal upon the indication of the event; and an audible indicator that receives the signal and provides to a user an audible indication of the event in response to the signal, the audible indication of the event being perceptible by a user without requiring the user to view a visual display of the uterine activity signal.

2. A medical device as set forth in claim 1, wherein the event is an onset of the uterine contraction.

3. A medical device as set forth in claim 1, wherein the event is a termination of the uterine contraction.

4. A medical device as set forth in claim 1, wherein the software further operates the processor to determine an indication of a second event relating to the uterine contraction based on a second change in incremental slope and to generate a second signal upon the indication of the second event, and wherein the audible indicator receives the second signal and provides to the user an audible indication of the second event in response to the second signal, the audible indication of the second event being perceptible by the user without requiring the user to view a visual display of the uterine activity signal.

5. A medical device as set forth in claim 4, wherein the first event is an onset of the uterine contraction and the second event is a termination of the uterine contraction.

6. A medical device as set forth in claim 1, wherein the software further operates the processor to determine an indication of a second event of the uterine contraction based on a second change in incremental slope and to terminate generation of the signal upon the indication of the second event.

7. A medical device as set forth in claim 6, wherein the first event is an onset of the uterine contraction and the second event is a termination of the uterine contraction.

8. A medical device as set forth in claim 1, wherein the uterine contraction has a maximum amplitude, wherein the software operates the processor to determine when the maximum amplitude occurs and to generate a second signal upon indication of the maximum amplitude, and wherein the audible indicator receives the second signal and provides to the user an audible indication of the maximum amplitude in response to the second signal, the audible indication of the maximum amplitude being perceptible by the user without requiring the user to view a visual display of the uterine activity signal.

9. A medical device as set forth in claim 8, wherein the software operates the processor to determine an indication of a second event relating to the uterine contraction based on a second change in incremental slope of the uterine activity signal and to generate a third signal upon the indication of the second event, and wherein the audible indicator receives the third signal and provides to the user an audible indication of the second event in response to the third signal, the audible indication of the second event being perceptible by the user without requiring the user to view a visual display of the uterine activity signal.

10. A medical device as set forth in claim 1, further comprising:
    a visual display capable of displaying the uterine activity signal.

11. A software program for indicating to a user the occurrence of a uterine contraction in a uterine activity signal obtained from a patient, the software indicating the uterine contraction by:
    obtaining the uterine activity signal;
    determining a change in incremental slope of the uterine activity signal;
    determining an occurrence of an event relating to the uterine contraction based on the change in incremental slope of the uterine activity signal;
    generating a signal upon the occurrence of the event;
    providing the signal to an audible indicator; and
    providing an audible indication of the occurrence of the event from the audible indicator to a user in response to the signal, the audible indication of the occurrence of the event being perceptible by the user without requiring the user to view a visual display of the uterine activity signal.

12. A software program as set forth in claim 11, wherein the event is a beginning of the uterine contraction.

13. A software program as set forth in claim 11, wherein the event is an ending of the uterine contraction.

14. A software program as set forth in claim 11, wherein the software program is implemented by a processor of a medical device having the audible indicator, and wherein the generated signal is provided to the audible indicator by the processor.

15. A software program as set forth in claim 14, the software program further indicating the uterine contraction by:
    determining an occurrence of a second event relating to the uterine contraction based on a second change in incremental slope of the uterine activity signal.

16. A software program as set forth in claim 15, wherein the second event is an ending of the uterine contraction.

17. A software program as set forth in claim 15, the software program further indicating the uterine contraction by:
    generating a second signal upon the occurrence of the second event.

18. A software program as set forth in claim 15, the software program further indicating the uterine contraction by:
    ceasing generation of the signal upon the occurrence of the second event.

19. A software program as set forth in claim 15, wherein the uterine contraction has a maximum amplitude, the software program further comprising:
    determining the occurrence of the maximum amplitude;
    generating a second signal in response to the occurrence of the maximum amplitude; and
    generating a third signal upon the occurrence of the second event.

* * * * *